United States Patent
Rehdorf et al.

(10) Patent No.: US 11,297,835 B2
(45) Date of Patent: Apr. 12, 2022

(54) AQUEOUS COMPOSITIONS OF PERILLIC ACID COMPOUNDS

(71) Applicant: B.R.A.I.N. BIOTECHNOLOGY RESEARCH AND INFORMATION NETWORK AG, Zwingenberg (DE)

(72) Inventors: Jessica Rehdorf, Bensheim (DE); Alice Kleber, Bensheim (DE)

(73) Assignee: BRAIN BIOTECH AG, Zwingenberg (DE)

( * ) Notice: Subject to any disclaimer, the term of this patent is extended or adjusted under 35 U.S.C. 154(b) by 0 days.

(21) Appl. No.: 16/072,336

(22) PCT Filed: Dec. 22, 2016

(86) PCT No.: PCT/EP2016/082421
§ 371 (c)(1),
(2) Date: Jul. 24, 2018

(87) PCT Pub. No.: WO2017/129339
PCT Pub. Date: Aug. 3, 2017

(65) Prior Publication Data
US 2019/0029254 A1 Jan. 31, 2019

(30) Foreign Application Priority Data
Jan. 29, 2016 (EP) .................................... 16153502

(51) Int. Cl.
*A61K 8/36* (2006.01)
*A01N 37/08* (2006.01)
(Continued)

(52) U.S. Cl.
CPC ................ *A01N 37/08* (2013.01); *A23L 2/52* (2013.01); *A23L 33/10* (2016.08); *A61K 8/062* (2013.01); *A61K 8/064* (2013.01); *A61K 8/36* (2013.01); *A61K 31/19* (2013.01); *A61K 47/10* (2013.01); *A61K 47/36* (2013.01); *A61Q 19/00* (2013.01); *A23V 2002/00* (2013.01)

(58) Field of Classification Search
CPC .............. A23L 2/44; A23L 33/10; A61K 8/36
See application file for complete search history.

(56) References Cited

U.S. PATENT DOCUMENTS

2010/0305214 A1 12/2010 D'Alessio
2014/0234398 A1* 8/2014 Zadini .................... A61K 31/01
424/450

FOREIGN PATENT DOCUMENTS

DE 10308278 A1 9/2004
DE 10335634 A1 3/2005
(Continued)

OTHER PUBLICATIONS

Written translation of WO 2004076400 A1 (2004), pp. 1-65 (Year: 2004).*
(Continued)

*Primary Examiner* — Craig D Ricci
*Assistant Examiner* — Janet L Coppins
(74) *Attorney, Agent, or Firm* — Hudak, Shunk & Farine Co. LPA (57) ABSTRACT

The present invention relates to compositions of perillic acid compounds, therapeutic and non-therapeutic uses of the compounds and compositions as well as a method of preparing the composition.

17 Claims, 3 Drawing Sheets

(51) Int. Cl.
*A61K 8/06* (2006.01)
*A61Q 19/00* (2006.01)
*A61K 47/36* (2006.01)
*A61K 47/10* (2017.01)
*A23L 33/10* (2016.01)
*A23L 2/52* (2006.01)
*A61K 31/19* (2006.01)

(56) References Cited

FOREIGN PATENT DOCUMENTS

| | | |
|---|---|---|
| EP | 3078310 A1 | 10/2016 |
| JP | 2005-132832 A | 5/2005 |
| WO | 03057193 A1 | 7/2003 |
| WO | WO-2004076400 A1 * 9/2004 ........... C07C 69/007 |

OTHER PUBLICATIONS

Wang et al, J. Food Protection, vol. 75 (10), 2012, pp. 1873-1877. (Year: 2012).*
Wang et al, J Food Protection: 2012, vol. 75 (10), pp. 1873-1877. (Year: 2012).*
Speelmans, G., et al., Appl. Microbiol Biotechnol, 1998, vol. 50, pp. 538-544.
Japanese Patent Office official action dated Nov. 26, 2020 for corresponding application JP 2018-539860.

* cited by examiner

AQUEOUS COMPOSITIONS OF PERILLIC ACID COMPOUNDS

FIELD OF THE INVENTION

The present invention relates to compositions of perillic acid compounds, therapeutic and non-therapeutic uses of the compounds and compositions as well as a method of preparing the composition.

BACKGROUND OF THE INVENTION

There is a constant need in the industry for substances that have preservative properties that can be used at very low amounts. These substances should be easy to produce, stable and available at high quality. Hundreds or even thousands of different preservatives are known in the art.

Perillic acid can be produced by conversion of limonene using a solvent-tolerant bacterial strain of Pseudomonas putida. An example for such a production process is given in Speelmans G et al., Appl Microbiol Biotechnol (1998) 50: 538-544.

Perillic acid and some derivatives are known from the art. DE 103 08 278 A1 describes perillic acid and its application as an active ingredient against microorganisms, including bacteria, yeasts and fungi. The use of perillic acid as preservative is described as well. However, no indication of the pH value of the compositions is described in DE 103 08 278 A1. The compositions used in this document are based on dimethyl sulfoxide and not water. Hence, the results shown therein cannot provide any useful information for practical use of compositions containing perillic acid and its derivatives. Specific compositions or useful salts of perillic acid are not disclosed.

US 2010/0305214 A1 describes the use of perillic acid to increase tissue repair and decrease inflammation in tissue. The examples relate to perillic alcohol and limonene only. Specific compositions are not described.

US 2014/0234398 A1 discloses pharmaceutical formulations and methods for treating atherosclerosis. The compositions comprise a bile acid and a terpene. The pharmaceutical preparations are administered in order to emulsify atherosclerotic plaque in an artery of a mammal. The perillic acid and its derivatives described in this prior art document serve as emulsifiers for the plaque. In other words the circumstances under which the compound is supposed to exert its effects is always the physiological pH, i.e. close to pH 7.4. Thus, the experiments were conducted at a pH of close to 7.4 as well. The document does not provide any hint that the activity of perillic acid could be increased by use at a pH condition below 7.

Figure 1A:
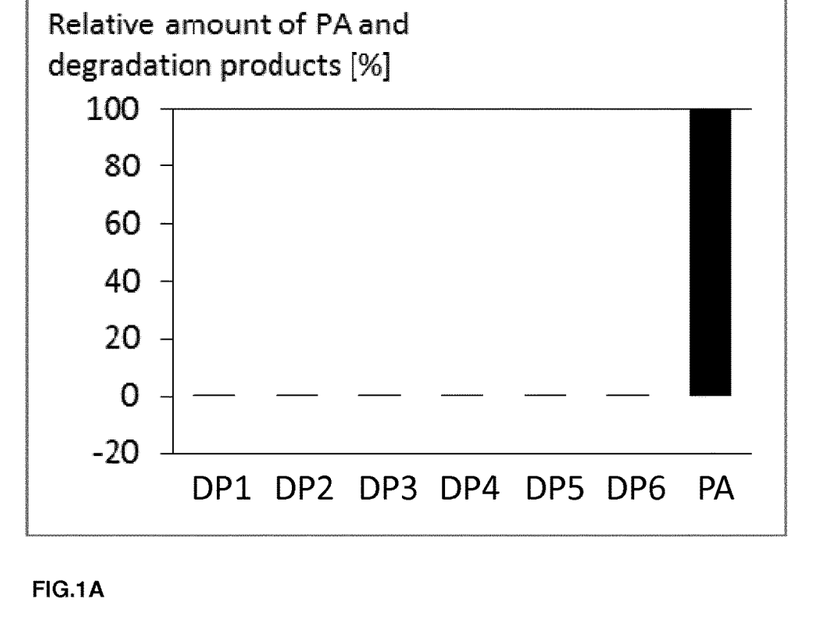
FIG. 1A: A diagram of the proportions of sodium perillate and its degradation products (DP1 to DP6) after 12 months of storage at room temperature.
Figure 1B:
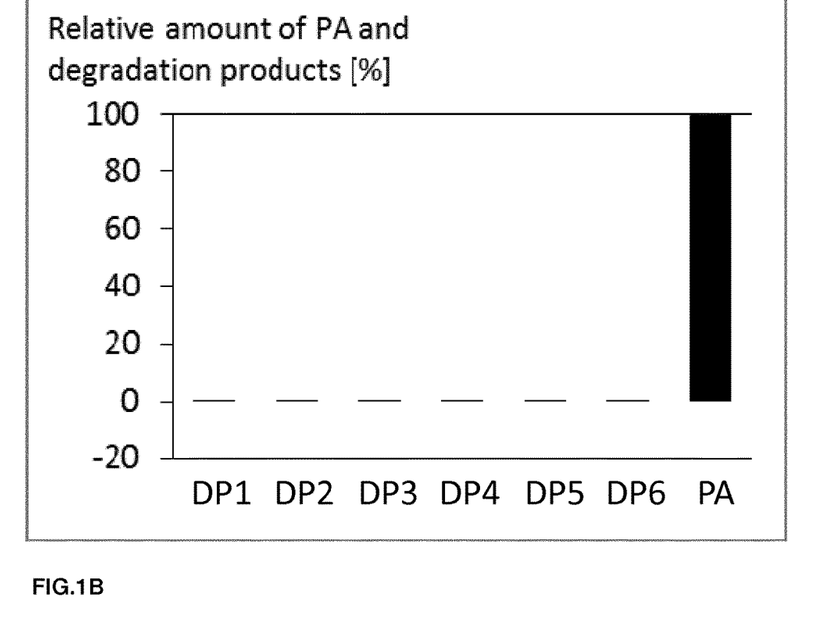
FIG. 1B: A diagram of the proportions of sodium perillate and its degradation products (DP1 to DP6) after 12 months of storage at 50° C.
Figure 2:
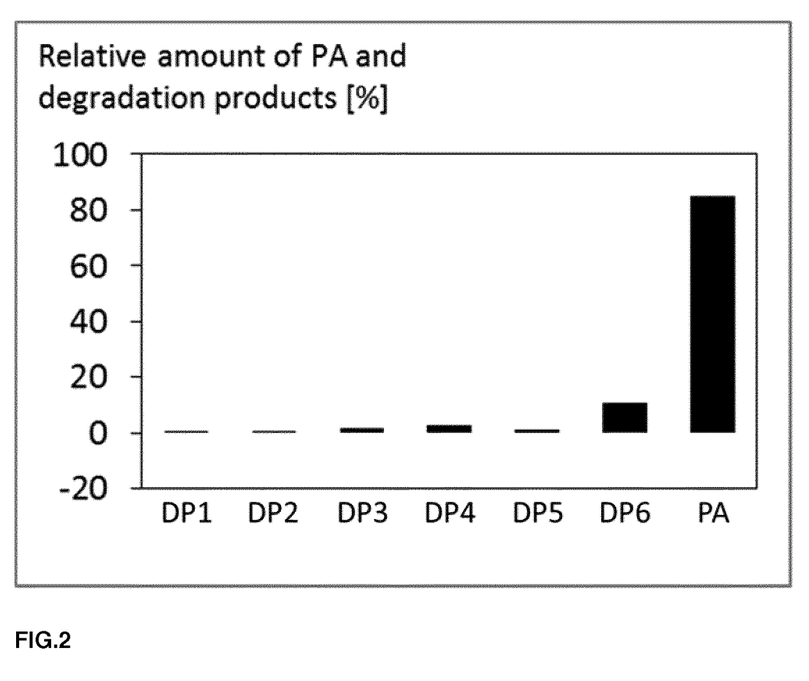
FIG. 2: A diagram of the proportions of perillic acid and its degradation products (DP1 to DP6) after 12 months of storage at room temperature.
Figure 3:
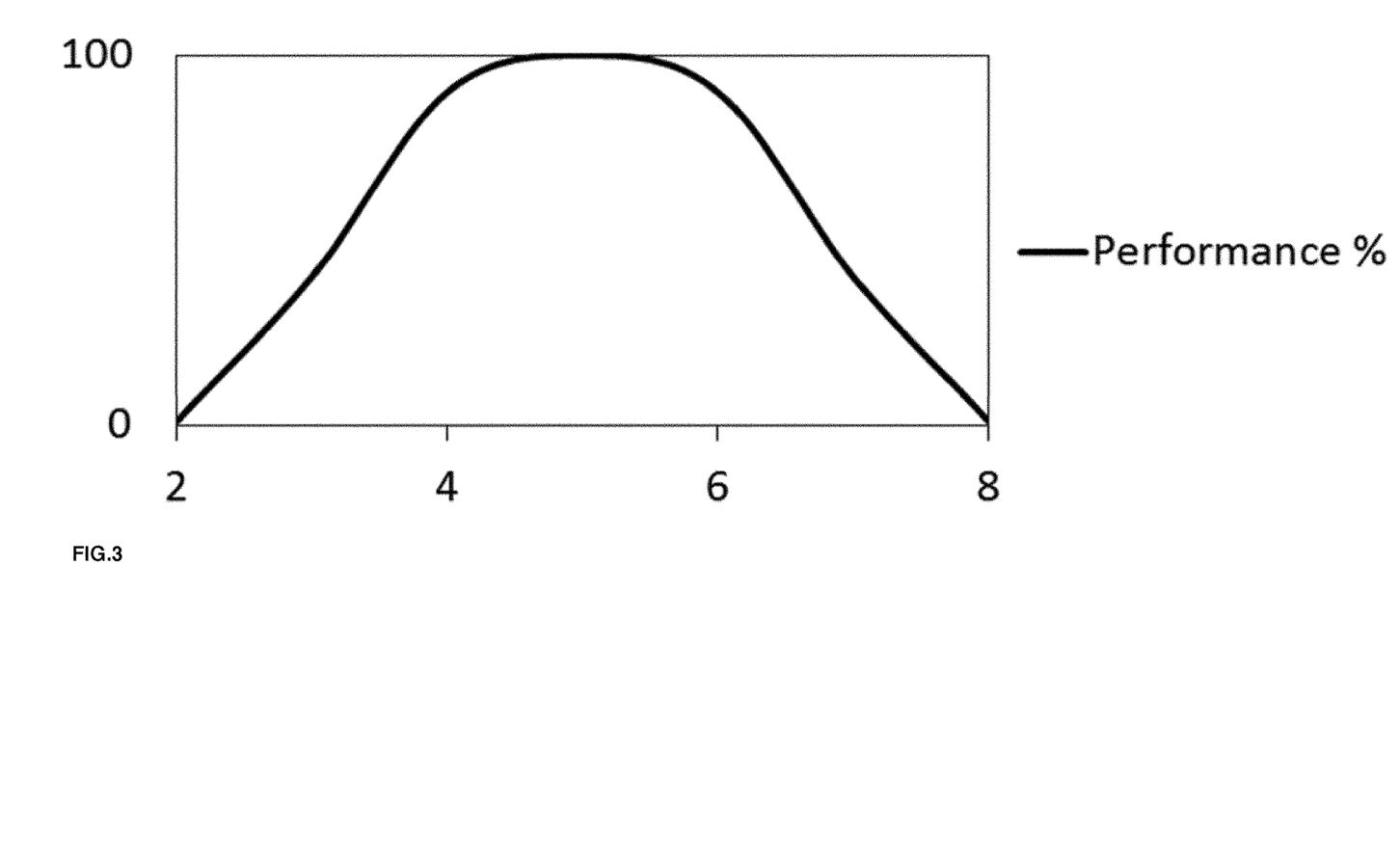
FIG. 3: The graph illustrates the relationship of the performance of perillic acid compounds and the influence of pH value on the performance of the compound. It can be seen that the performance, i.e. the antimicrobial efficacy, of a given amount of perillic acid compound will vary significantly with changing pH value. Maximum performance is observed between pH 4 and 6.

DE 103 35 634 A1 mentions perillic acid and its use in different formulations. None of these formulations has a pH value in the range required by the present invention and there was no reason for the skilled person to expect that a small decrease in pH could boost the activity of perillic acid as illustrated in FIG. 3 of this application, showing a maximum performance at about pH 4 to 6.

EP 3 078 310 A1 discloses compositions for the preparation of decalcifying solutions that include perillic acid. The compositions are in the form of granules or powders. Generally, decalcifying compositions have very low pH values below pH 2.

Three major issues have prevented the widespread use of perillic acid compounds in the art. Perillic acid compounds have limited solubility in water and had to be used in rather high amounts to be effective and the stability of the active compound was limiting. Thus, the high amounts required to achieve the desired effect could not be dissolved in aqueous compositions because of the low water solubility of the compound. One approach that has been tried before is derivatization of perillic acid in order to improve efficacy and/or solubility thereof.

SUMMARY OF THE INVENTION

It is an object of the invention to provide compositions that are resistant to microbial spoilage for a very long period while containing only very small proportions of preservatives.

The inventors of the present invention have now found that the compositions of this invention effectively increase the activity of perillic acid compounds, their solubility in water and the shelf life of compositions that contain the compounds. The inventors have also shown that specific perillic acid compounds have very high stabilities when compared to other perillic acid compounds. Thus, the compositions of this invention may contain relatively small amounts of perillic acid compounds.

DETAILED DESCRIPTION OF INVENTION

Compositions

In an aspect the present invention relates to a composition comprising at least one perillic acid compound selected from the group consisting of perillic acid, one or more salts of perillic acid, one or more hydrolysable esters of perillic acid, one or more hydrolysable ethers of perillic acid, and/or derivatives thereof, and water, wherein the composition has a pH in the range of from 2 to <7.

It has now surprisingly been found that the compounds of this invention have significantly increased activity when used at the appropriate pH level and the compounds effectively prolong shelf lives of products that contain the compounds at the appropriate pH level. Heretofore perillic acid compounds have not widely been used in compositions because of lack of long term stability of the perillic acid compound and large amounts of compound being necessary to achieve the desired effects. Long term stability of perillic acid compounds is particularly important when the compound is used as a preservative. Preservatives are used to impart long term stability to compositions. Hence, the compounds themselves should be stable. It has now been found that setting the pH value in a composition in a range according to the present invention provides long term stability to the composition, while perillic acid compounds can be used in comparatively low amounts. In particular, the antimicrobial performance of the perillic acid compounds of this invention is increased to such an extent that the limited solubility of the compounds is not restricting the use of the compound in the desired pH range.

Of course, long term stability is bestowed on the composition even if the perillic acid compound is not used for that specific purpose. The composition will profit from the preservative function of the compound in any case.

The desired pH range also provides for improved solubility and antimicrobial efficacy of the perillic acid compounds. If the pH is set in the inventive pH range, a balanced combination of high antimicrobial activity and solubility is achieved. In this description all measurements are conducted at 20° C. unless otherwise indicated or required by the method.

The compositions of this invention preferably contain the perillic acid compound in an amount of from 0.00001 to 10% (w/v), more preferably from 0.0001% to 2% (w/v) and most preferably from 0.001 to 1% (w/v). More preferably the compound is contained in amounts ranging from 0.01% to 0.8% (w/v) of the total composition. The inventors have found that the perillic acid compounds of this invention can be used at very low concentrations in the pH range of this invention because antimicrobial activity is largely in-creased. For example, the present invention allows for the use of perillic acid compounds with very high antimicrobial activity at a concentration of the perillic acid compound of less than 2% (w/v), particularly less than 1% (w/v) or even less than 0.8% (w/v). in preferred embodiments the amount of perillic acid compound is even less than 0.5% (w/v) or less than 0.2% (w/v).

The inventors have now found that the antimicrobial efficacy of perillic acid compounds is remarkably pH dependent. If a certain amount of perillic acid compound is used, it will be most efficacious in a pH range of 2 to <7, even more efficacious at a pH of 3 to <7 or 4 to <7 and most efficacious at a pH of 4.5 to 6.5. A desirable pH is at least 2, more particularly at least 3, preferably at least 4 and most preferred at least 4.5. At a pH be-low the desired value the efficacy of the compound will strongly decrease again. If the pH is too high, the efficacy will decrease as well. Thus, the pH should be less than 7, preferably less than 6.7, more preferably less than or equal to 6.5, and most preferably less than or equal to 6. Hence, if used at the most effective pH, the total amount of perillic acid compound in the compositions can be reduced.

In preferred embodiments, the maximum amount of perillic acid compound (w/v) used in the compositions is determined according to the following equation: cPA=0.1% (w/v)*InpH±25%

Using this equation to find the correct amount of perillic acid compound for a specific composition will lead to optimized efficacy of the compound. It is surprising that the antimicrobial perillic acid performance shows such extraordinary pH dependence. In preferred embodiments, the amount of perillic acid compound used in the compositions of this invention is in the area of from 0.0001 to 0.2% (w/v) in a pH range of from 4.5 to 5.5. This illustrates that the amount of perillic acid can be set to extremely low values in the optimized pH range. In the prior art, concentrations of up to 10% by weight have been suggested. However, such high amounts are not soluble in water.

The perillic acid compound is selected from the group consisting of perillic acid, salts of perillic acid, hydrolysable esters of perillic acid, hydrolysable ethers of perillic acid, and/or derivatives thereof. In a preferred embodiment, the perillic acid compound is selected from perillic acid and its salts, in particular its alkali metal salts. A preferred perillic acid compound is perillic acid. The perillic acid compound is preferably selected from the salts of perillic acid, in particular the ammonium, alkali metal and alkaline earth metal salts. The present inventors have found that the salts of perillic acid, in particular the alkali metal and alkaline earth metal salts exhibit superior long-term stability. In preferred embodiments, the perillic acid compound is selected from perillic acid, sodium perillate, potassium perillate, ammonium perillate, calcium perillate, magnesium perillate and mixtures thereof. In particularly preferred embodiments the perillic acid compound is selected from perillic acid and sodium perillate.

The perillic acid salts also have the advantage that they serve as a buffer system in the composition, in particular when perillic acid is present in the composition together with a salt of perillic acid such as an ammonium, alkali metal and/or alkaline earth metal salt. In preferred embodiments, it is not necessary that any other buffer is added to the composition, in particular if the buffering properties of perillic acid are used. Preferably, the compositions of this invention do not contain any buffer, in particular no bicarbonate buffer. When the pH of the composition is set to optimized values the buffering capacity of perillic acid compounds is maximized.

The perillic acid compound is preferably used in the form of its R-enantiomer, its S-enantiomer or any mixture thereof, including racemic mixtures.

It is believed that the pH value of the compositions of this invention provides for a higher activity, solubility and stability of the perillic acid compound. The pH of the compositions of this invention preferably is from acidic, i.e. pH 2, to slightly alkaline, i.e. less than pH 7. It is believed that the pH provides for a relevant portion of the perillic acid compound being protonated and thereby more hydrophobic than the deprotonated form of the perillic acid compound. Thereby, the compound can more easily pass through membranes of cells. Still in this range a relevant amount is deprotonated and the charged molecule has good solubility in water. The pH range of this invention provides for an optimized composition with regard to solubility, efficacy and stability of the perillic acid compound. The inventors have conducted many experiments to find the concentration where the perillic acid compound has good solubility in water and still shows a high antimicrobial activity against relevant bacteria, fungi and yeasts. The experiments in the experimental section below show activity of the perillic acid compounds and compositions against a selection of microorganisms. The conservation efficacy tests show that the activity is sufficient to exert a strong preserving effect.

The inventors have found that a further optimization with regard to improved preserving properties can be achieved by adjusting the pH value to a range of from pH 3 to <7. Adjusting the pH value to less acidic values increases the amount of deprotonated perillic acid compound in the composition. The inventors found out that this further increases shelf life of the compositions that contain perillic acid compounds as preservatives, as the solubility is increased at higher pH while maintaining efficacy of the perillic acid compound at a high level. An optimized pH range is from 4 to <7, in particular from 4.5 to 6.5, or up to 6. It has also been found that solubility and efficacy of the perillic acid compound is increased at the indicated pH values. The extent to which the efficacy of perillic acid compounds is increased by pH adjustment is remarkable and surprising.

The compositions of this invention contain water. Microorganisms need water to grow. Thus, water containing compositions are prone to microbial spoilage. The compositions of this invention provide a way of preserving water containing compositions in an effective way. Preferred compositions of this invention are water-based. In the context of this invention, "water-based" means that water is the main ingredient in the composition, i.e. the ingredient that is present in the highest proportion when compared with the other ingredients in the composition. In preferred embodiments the amount of water in the compositions of this invention is at least 10% by weight, or at least 20% by weight of the composition, more preferred at least 30% by weight, more preferred at least 40% by weight, more preferred at least 50% by weight or at least 70% by weight, or even at least 75% by weight.

In particular embodiments, the compositions of this invention are compositions wherein water or an aqueous solution forms a continuous phase. This is true for aqueous sus-pensions and oil-in-water emulsions and water-in-oil emulsions. These emulsions are notoriously difficult to protect against microbial spoilage. Perillic acid compounds of this invention are excellent preservatives for such compositions, if an appropriate pH is used. Other compositions that are within the scope of this invention are compositions that contain surfactants.

In preferred embodiments, the composition of this invention is selected from foodstuffs, food packaging, beverages, animal food, medicinal products, pharmaceutical products, cosmetic products, household products, plant protection, industrial and technical products. Suitable foodstuffs include water-containing foodstuffs, in particular dairy products such as yogurt, curd, cheese, cottage cheese, grating cheese; but also marmalade, jelly. Suitable food packaging includes water-containing food packaging and food pack-aging that has been surface-treated with the compositions of the invention. It also includes shells, envelopes, casings, rinds and wrappings within which food can be or is packaged. Preferred embodiments include food packaging for cheese and sausage products, including cheese rinds and sausage casings. Suitable beverages include carbonated and non-carbonated beverages, in particular lemonade, beer, sparkling water, mineral water, energy drinks, milk, fruit juice, vegetable juice, smoothies and drinking yogurt, but also wine, sparkling wine, fruit wine, liquor and spirits. Suitable animal food includes water-containing animal food and pet food. Suitable medical devices include medical devices of class IIa. Preferred embodiments include water-containing medicinal products, in particular wound dressings and wound cleansing products and contact lenses solutions. Suitable pharmaceutical products include water-containing pharmaceutical products. Preferred embodiments include eye drops, nose drops, aerosols, in-fusions, injections, solutions, emulsions, dispersions, pastes, gels, ointments, capsules, and effervescent formulations. Preferred cosmetic products include water-containing cosmetic products. Preferred embodiments include creams, lotions, ointments, deodorant sticks, pump sprays, toothpaste, mouth wash, shampoo, soap, shower gel, aerosols, sprays, solutions, emulsions, dispersions and pastes. Preferred household products include water-containing household products, in particular those used for cleaning or maintenance of water-using household appliances like washing machines, dish washers, driers, coffee machines, steam cookers etc. Preferred embodiments include detergents, washing agents and cleaning agents. Preferred technical products include water-containing technical products. Preferred embodiments include paints, lacquers, lubricants, coatings, construction materials, sealing mass, adhesives, paste and glue.

The compositions of this invention preferably comprise limonene in a concentration of less than 50 mM, preferably less than 25 mM and more preferably less than 10 mM. In preferred embodiments the compositions of this invention do not comprise any limonene in detectable amounts.

The compositions of this invention are preferably containing only very few microorganisms. The compositions of this invention contain the perillic acid compound in order to provide for excellent microbial quality. Therefore, the total amount of bacteria present in the compositions preferably is below 10.000, more preferably below 1.000, most preferably below 100 cfu/mL, this is in particular true for Pseudomonas putida bacteria.

The compositions may additionally comprise at least one activity enhancing substance that enhances the anti-microbial activity of the perillic acid compound. It has been found that combination of the perillic acid compound and the activity enhancing substance in the compositions of the present invention is accompanied by a surprising synergistic effect so that effective inhibition of microbial growth can be achieved at extremely low concentrations of both perillic acid compound and activity enhancing substance.

Preferably, the amount (w/v) of activity enhancing substance in the compositions of the present invention is at least 10% of the amount of perillic acid compound in the compositions. More preferably, the amount (w/v) of activity enhancing substance in the compositions of the present invention is at least as high as the amount (w/v) of perillic acid compound in the compositions. More preferably, the amount of activity enhancing substance is at least twice as high, more preferably at least three times as high, more preferably at least four times as high, more preferably at least five times as high, even more preferably at least ten times as high as the amount of perillic acid compound in the compositions. However, the amount of activity enhancing substance should also not be too high. Preferably, the amount of activity enhancing substance in the compositions is at most 1000 times, more preferably at most 500 times, more preferably at most 100 times, more preferably at most 50 times, more preferably at most 35 times, more preferably at most 20 times as high as the amount of perillic acid compound in the compositions.

The preferred ratio of the amount (w/v) of activity enhancing substance in the compositions to the amount (w/v) of perillic acid compound in the compositions may vary de-pending on the activity enhancing substance. For example, when the activity enhancing substance is a 1,2-diole, the ratio of the amount of activity enhancing substance to the amount of perillic acid compound is preferably in the range of from 0.1 to 50, more preferably of from 1 to 10. When the activity enhancing substance is a carboxylic acid, the ratio of the amount of activity enhancing substance to the amount of perillic acid compound is preferably in the range of from 1 to 100, more preferably of from 5 to 50. When the activity enhancing substance is an aromatic alcohol, the ratio of the amount of activity enhancing substance to the amount of perillic acid compound is preferably in the range of from 2 to 200, more preferably of from 5 to 50.

Preferably, the activity enhancing substance is an organic compound. Preferably, the organic compound comprises at least two carbon atoms, more preferably at least three carbon atoms, more preferably at least four carbon atoms, more preferably at least five carbon atoms, more preferably at least six carbon atoms, more preferably at least seven carbon atoms, more preferably at least eight carbon atoms. However, the organic compound should not be too large. Otherwise, the solubility of the organic compound might be too low. Therefore, the organic compound comprises preferably at most 16 carbon atoms, more preferably at most 12 carbon atoms, more preferably at most 10 carbon atoms.

Preferably, the activity enhancing substance comprises at least one terminal oxygen residue. In one embodiment, the activity enhancing substances might be mono-alcohols, preferably aromatic mono-alcohols. Preferred mono-alcohols are selected from 2-phenoxyethanol, 2-phenylethanol and benzyl alcohol.

However, it turned out that more preferably the activity enhancing substance comprises at least two terminal oxygen residues. Preferably, the activity enhancing substance comprises exactly two terminal oxygen residues. In alternative embodiments, the activity enhancing substance comprises more than two terminal oxygen residues. In such alternative embodiments, the activity enhancing substance comprises preferably exactly three terminal oxygen residues. In less preferred alternative embodiments, the activity enhancing substance comprises preferably six terminal oxygen residues, more preferably five terminal oxygen residues, more preferably four terminal oxygen residues.

A terminal oxygen residue according to the present invention is an oxygen residue that is covalently bound to exactly one carbon atom within the organic compound. Terminal oxygen residues might additionally also be bound to hydrogen. However, preferably the activity enhancing substance comprises at most two hydroxyl groups. The following scheme shows examples of terminal oxygen residues, wherein R represents an arbitrary group bound to the terminal oxygen residue(s) via carbon to oxygen bonds.

In contrast to terminal oxygen residues, oxygen residues that are covalently bound to two carbon atoms are termed bridging oxygen residues according to the present invention. The following scheme shows a bridging oxygen residues, wherein R and R' represent arbitrary groups bound to the bridging oxygen residue via carbon to oxygen bonds.

Preferably, the terminal oxygen residues are present in the activity enhancing substance in close proximity. "Being present in close proximity" means according to the present invention that the terminal oxygen residues are bound to carbon atoms that are spaced by at most two, more preferably by at most one carbon atom that is not bound to a terminal oxygen residue. More preferably, the terminal oxygen residues are bound to adjacent carbon atoms or even to the same carbon atom. Terminal oxygen residues that are bound to adjacent carbon atoms or to the same carbon atom within the activity enhancing substance form a terminal oxygen group (TO-group) together with the corresponding carbon atoms and optional hydrogen residues according to the present invention. The inventors hypothesize that the presence of a TO group is important to achieve the desired synergistic effect. Examples of TO-groups are shown in the following scheme, wherein R represents an arbitrary group bound to the TO-group via a carbon to carbon bond and R' represents an arbitrary group bound to terminal oxygen residues via carbon to oxygen bonds. Specific examples of TO groups include the vicinal diol group, the α-hydroxyl ketones and the carboxylic acid group.

Preferably, the terminal oxygen residues are present in the activity enhancing substance in form of at least one TO-group. According to the present invention, a TO-group comprises at least two terminal oxygen residues, which are present in geminal position or in vicinal position, i.e., terminal oxygen residues bound to the same (geminal) or to adjacent (vicinal) carbon atoms within the activity enhancing substance. In alternative embodiments, the terminal oxygen residues are not present in form of TO-groups. In such alternative embodiments, the terminal oxygen residues are present in isolated form, i.e. the terminal oxygen residues are bound to carbon atoms that are not directly bound to each other.

Preferably, the TO-group is selected from the group consisting of the malic group, the glycol group and the carboxyl group as explained below. More preferably, the TO-group is selected from the group consisting of the glycol group and the carboxyl group. Preferably, the glycol group is a terminal glycol group.

Hence, the activity enhancing substance is preferably selected from the group consisting of 1,2-diols, carboxylic acids and derivatives thereof. More preferably, the activity enhancing substance is selected from the group consisting of alkane-1,2-diols, carboxylic acids and derivatives thereof. More preferably, the activity enhancing substance is selected from the group consisting of hexane-1,2-diol, octane-1,2-diol, decane-1,2-diol, levulinic acid, p-anisic acid, propionic acid, pelargonic acid, malic acid, sodium benzoate and potassium sorbate. Even more preferably, the activity enhancing substance is selected from the group consisting of octane-1,2-diol, levulinic acid, sodium benzoate and potassium sorbate.

Preferably, the activity enhancing substance comprises exactly one TO-group. In alter-native embodiments, the activity enhancing substance comprises at least two TO-groups, preferably exactly two TO-groups. Preferably, the activity enhancing substance comprises at most three TO-groups.

According to the present invention, a TO-group with terminal oxygen residues in vicinal position might comprise three terminal oxygen residues. For example, a carboxyl group (C(O)OH) might be bound to a carbon atom that is bound to a hydroxyl group. A preferred activity enhancing substance comprising such TO-group is malic acid. Therefore, such TO-group is termed "malic group" according to the present invention.

However, preferably, TO-groups comprise exactly two terminal oxygen residues according to the present invention. An especially preferred TO-group with terminal oxygen residues in vicinal position is the glycol group (C(OH)C(OH)). Especially preferably, the TO-group is a terminal glycol group, i.e. a glycol group, in which at least one of the carbon atoms is not bound to a second carbon atom. Preferably, activity enhancing substances that comprise a glycol group do not comprise any further terminal oxygen residues. Preferred activity enhancing substances comprising such TO-group are 1,2-diols. Especially preferred activity enhancing substances are alkane-1,2-diols. Preferably, the alkane-1,2-diols have at least 6 carbon atoms. Preferably, the alkane-1,2-diols have at most 12 carbon atoms. Preferably, the alkane-1,2-diols are selected from the group consisting of hexane-1,2-diol, octane-1,2-diol and decane-1,2-diol. More preferably the alkane-1,2-diol is octane-1,2-diol.

More preferred than TO-groups with terminal oxygen residues in vicinal position are TO-groups with terminal oxygen residues in geminal position. Most preferred, the TO-group with terminal oxygen residues in geminal position is a carboxyl group. Preferably, the activity enhancing substance comprises at most two carboxyl groups, more preferably at most one carboxyl group.

Preferred activity enhancing substances are selected from organic acids, particularly carboxylic acids, and derivatives thereof. According to the present invention, derivatives of carboxylic acids are preferably selected from the group consisting of salts of carboxylic acids, hydrolysable esters of carboxylic acids, and/or hydrolysable ethers of carboxylic acids. In a preferred embodiment, the derivatives of carboxylic acids are salts thereof, in particular their alkali metal salts. Derivatives of carboxylic acids are preferably selected from the group consisting of ammonium, alkali metal and alkaline earth metal salts thereof. Sodium, potassium, ammonium, calcium and magnesium salts are more preferred. In particularly preferred embodiments the derivatives of carboxylic ac-ids are sodium or potassium salts thereof.

Preferably, the carboxylic acids are monoacids. Preferably, the carboxylic acids have a molecular weight of more than 50 g/mol, more preferably more than 65 g/mol, more preferably more than 75 g/mol, more preferably more than 100 g/mol. Preferably, the carboxylic acids have a molecular weight of less than 250 g/mol, more preferably less than 200 g/mol, more preferably less than 160 g/mol, more preferably less than 150 g/mol Preferably, the carboxylic acids have a pKa of at least 2.5 more preferably at least 3.0, more preferably at least 3.5, more preferably at least 4.0. Preferably, the carboxylic acids have a pKa of at most 6.5, more preferably, at most 6.0, more preferably at most, 5.5, more preferably at most 5.0.

Preferably, the carboxylic acids are selected from the group consisting of levulinic acid, p-anisic acid, propionic acid, pelargonic acid, malic acid, benzoic acid and sorbic acid. More preferably, the carboxylic acids are selected from the group consisting of levulinic acid, p-anisic acid, propionic acid, pelargonic acid, benzoic acid and sorbic acid. Even more preferably, the carboxylic acids are selected from the group consisting of levulinic acid, benzoic acid and sorbic acid.

Uses of Perillic Acid Compounds and Compositions

The compositions of this invention are useful for a large number of applications. In an aspect of this invention, perillic acid compounds as defined herein can be used for preservation, for prevention against microbial spoilage, for therapeutic treatment against microbial infection, for cosmetic treatment and/or care against microbial infection, as fungicides, or as herbicides.

Irrespective of the specific use, the perillic acid compounds will preferably be used in an amount of from 0.00001% to 10% (w/v), more preferably from 0.0001% to 2% (w/v), more preferably from 0.001% to 1% and most preferred from 0.01% to 0.8% (w/v) of the total composition within which it is used. The maximum amount may be as low as <0.5% (w/v) or <0.2% (w/v).

The product or composition in or on which the perillic acid compound or composition is used preferably has a pH value from 2 to <7, preferably in a range of from pH 3 to <7. Adjusting the pH value to less acidic values increases the amount of deprotonated perillic acid compound in the composition. The inventors found that this further increases the preserving effect of the perillic acid compounds in the compositions. An optimized pH range is from 4 to <7, in particular from 4.5 to 6.5, or up to 6. It has also been found that solubility of the perillic acid compound is increased at the indicated pH values.

Preservation

In preferred embodiments the perillic acid compounds of this invention are used for preservation. This may include preservation of compositions according to this invention. Compositions that can be preserved using the perillic acid compound of this invention include foodstuffs, food packaging, beverages, animal food, medicinal products, pharmaceutical products, cosmetic products, household products, plant protection, industrial and technical products.

Foodstuffs that can be preserved using the perillic acid compounds of this invention include water-containing foodstuffs, in particular dairy products such as yogurt, curd, cheese, cottage cheese, grating cheese; but also marmalade, and jelly. Other embodiments include preservation of sea food such as lobsters, oysters, mussels, fish and shrimps. In order to achieve the desired preserving affect the perillic acid compound and/or the compositions of this invention are preferably added to the foodstuff or applied to the foodstuff.

Food packaging that can be preserved using the perillic acid compounds of this invention includes shells, envelopes, casings, rinds and wrappings within which food can be or is packaged. Preferred embodiments include food packaging for cheese and sausage products, including cheese rinds and sausage casings. In order to achieve the desired preserving affect the perillic acid compound and/or the compositions of this invention are preferably added to or applied to the food packaging.

Beverages that can be preserved using the perillic acid compounds of this invention include carbonated and non-carbonated beverages, in particular lemonade, beer, sparkling water, mineral water, energy drinks, milk, fruit juice, vegetable juice, smoothies and drinking yogurt, but also wine, sparkling wine, fruit wine, liquor and spirits. In order to achieve the desired preserving affect the perillic acid compound and/or the compositions of this invention are preferably added to the beverage.

Animal food that can be preserved using the perillic acid compounds of this invention include water-containing animal food. Preferred embodiments include animal food in particular pet food. In order to achieve the desired preserving affect the perillic acid compound and/or the compositions of this invention are preferably added to the animal food.

Medical devices that can be preserved using the perillic acid compounds of this invention include medical devices of class Ha. Preferred embodiments include water-containing medicinal products, in particular wound dressings and wound cleansing products and contact lenses solutions. In order to achieve the desired preserving affect the perillic acid compound and/or the compositions of this invention are preferably added to or applied to the medicinal product.

Pharmaceutical products that can be preserved using the perillic acid compounds of this invention include water-containing pharmaceutical products. Preferred embodiments include eye drops, nose drops, aerosols, infusions, injections, solutions, emulsions, dispersions, pastes, gels, ointments, capsules, and effervescent formulations. In order to achieve the desired preserving affect the perillic acid compound and/or the compositions of this invention are preferably added to the pharmaceutical product.

Cosmetic products that can be preserved using the perillic acid compounds of this invention include water-containing cosmetic products. Preferred embodiments include creams, lotions, ointments, toothpaste, deodorant sticks, pump sprays, mouth wash, shampoo, soap, shower gel, aerosols, sprays, solutions, emulsions, dispersions and pastes. In order to achieve the desired preserving affect the perillic acid compound and/or the compositions of this invention are preferably added to the cosmetic composition.

Household products that can be preserved using the perillic acid compounds of this invention include water-containing household products, in particular those used for cleaning or maintenance of water-using household appliances like washing machines, dish washers, driers, coffee machines, steam cookers etc. Preferred embodiments include detergents, washing agents and cleaning agents. In order to achieve the desired preserving affect the perillic acid compound and/or the compositions of this invention are preferably added to the household product.

Technical products that can be preserved using the perillic acid compounds of this invention include water-containing technical products. Preferred embodiments include paints, lacquers, lubricants, coatings, construction materials, sealing mass, adhesives, paste and glue. In order to achieve the desired preserving affect the perillic acid compound and/or the compositions of this invention are preferably added to the technical product.

The perillic acid compounds of this invention are particularly useful for preservation of water-containing products. Preferably, the water content in the compositions, wherein the perillic acid compound or composition is used for purposes of preservation is at least 10% by weight, preferably at least 20% by weight, more preferred at least 40% by weight, more preferred at least 60% by weight, or at least 70% by weight and most preferred at least 75% by weight. In particular embodiments, the water-containing products are compositions wherein water or an aqueous solution forms a continuous phase. This is true for aqueous suspensions and oil-in-water emulsions and water-in-oil emulsions. Oil-in-water emulsions are notoriously difficult to protect against microbial spoilage. Perillic acid compounds of this invention are excellent preservatives for such compositions, if an appropriate pH is used. Other water-containing products that are within the scope of this invention are compositions that contain surfactants.

In preferred embodiments the perillic acid compounds or compositions of this invention are used as preservatives in emulsions. Emulsions are difficult media with regard to preservation because they comprise a lipophilic and a hydrophilic phase. Many preservatives are lipophilic and thereby accumulate in the oil phase of an emulsion. However, the phase that is most prone to bacterial spoilage is the aqueous or hydrophilic phase. The inventors have found that due to the adjustment of the pH to the desired range the preservation efficacy of the inventive preservative is maximized in emulsions.

Antimicrobial Uses

The perillic acid compounds and compositions of this invention can be used as antimicrobial agents and compositions. It has been shown that the compounds and compositions of this invention are active against bacteria, yeast and moulds. It is hence a preferred embodiment of this invention to use the perillic acid compounds and compositions as antimicrobial agents. Antimicrobial use includes therapeutic use and non-therapeutic use.

Therapeutic Use

In an embodiment, the perillic acid compounds or compositions are used as an antimicrobial agent in a therapeutic method. In other words, the compositions and compounds of this invention are preferred for use in a therapeutic method. The method preferably includes the step of administering to a subject an effective amount of the perillic acid compound or of the composition of this invention. Administration can be topical, local and/or systemic. The subject can be human or non-human. Preferred subjects are mammals, in particular humans. In preferred embodiments, the therapeutic method does not include cancer-therapy. In preferred embodiments, the compositions of this invention do not include compositions for use in the treatment of cancer.

Pathological conditions that can be treated with the perillic acid compounds and compositions of this invention include mycotic infections, bacterial infections and inflammation. Preferred pathological conditions include athlete's foot, nail fungus, eczema, rosacea and caries.

Therapeutic use includes the antimicrobial application against nosocomial infections, including those caused by MRSA, MRSE, ESBL and VRE. In another embodiment the use of the compounds and compositions against nosocomial infections, including those caused by MRSA, MRSE, ESBL and VRE, is not therapeutic but includes application as cleansers or disinfectants.

Non-Therapeutic Use

In an embodiment, the perillic acid compounds or compositions are used as an antimicrobial agent in a non-therapeutic method. The method preferably includes the step of administering to a subject or applying to an object an effective amount of the perillic acid compound or of the composition of this invention. Administration to a subject can be topical, local and/or systemic. Application to an object can be superficial, by admixture, coating, immersion or impregnation.

The subject can be human or non-human. Preferred subjects are mammals, in particular humans. The compounds and compositions of this invention can be used for improvement of skin balance and sebum control. Non-pathological conditions that can be treated with the perillic acid compounds and compositions of this invention include cosmetic conditions like halitosis, dandruff, rosacea, impure and large pore skin, couperose, body odor, and acne.

The non-therapeutic use includes application of the perillic acid compound or composition to an object. The object can be furniture, wood, stone, metal, construction material, surfaces in cars, factories and houses, filters in air conditioners and others.

The perillic acid compounds and compositions of this invention can also be used as herbicides and fungicides, in particular in plant protection products.

The compounds and compositions of this invention can be used as disinfectants in hospitals, restaurants, hotels, laundries, households, industry, animal farming etc.

Method

The invention also includes a method of preparing a composition according to this invention including the steps of preparing a mixture of a perillic acid compound and water, and optionally adjusting the pH to a value that is preferred for the compositions of this invention, in particular from 2 to <7, preferably to a range of from pH 3 to <7. Adjusting the pH value to less acidic values increases the amount of deprotonated perillic acid compound in the composition. The inventors found that this further increases the preserving effect on the compositions while maintaining efficacy of the perillic acid compound at high levels. An optimized pH range is from 4 to <7, in particular from 4.5 to 6.5, or up to 6. It has also been found that solubility of the perillic acid compound is in-creased at the indicated pH values.

EXAMPLES

Salts of Perillic Acid, in Particular Sodium Perillate

The invention comprises the application of alkali salts of perillic acid, particularly of sodium perillate, to stabilize various compositions in the range of pH 2 to <7 containing water as main constituent, and to address different application fields where microbial spoilage/growth is an issue. Beyond, sodium perillate shows a high long-term stability in both as a solid and in water-based systems, especially when exposed to thermal stress.

and *Staphylococcus aureus*), at 28° C. (*Candida albicans*) and at 25° C. (*Aspergillus brasiliensis*). Plates were evaluated after 24 h and 72 h, respectively. The minimal inhibitory concentration is defined as the concentration where no microbial growth was observed after 24 h and 72 h incubation at the specified temperature.

Table 1 Determination of the minimal inhibition concentration (MIC, % w/v) of sodium perillate against five classical spoiling organisms under acidic (pH<6.5) and alkaline (pH>7.5) conditions using the microdilution method adapted according to DIN EN ISO 20776-1:2006. The experiments were performed in micro-well plates in a final volume of 200 µL. MIC-values are given according to the following letter code. A>1% w/v, B=0.5-1% w/v, C=0.1-0.5% w/v. D<0.1% w/v.

|  | MIC in % w/v Microbial strains | | | | | | | | | |
|---|---|---|---|---|---|---|---|---|---|---|
|  | *Escherichia coli* | | *Pseudomonas aeruginosa* | | *Staphylococcus aureus* pH | | *Candida albicans* | | *Aspergillus brasiliensis* | |
|  | >7.5 | <6.5 | >7.5 | <6.5 | >7.5 | <6.5 | >7.5 | <6.5 | >7.5 | <6.5 |
| Sodium Perillate | B | C | A | B | B | D | C | D | n.a. | D |
| R-Perillic Acid | B | C | A | B | B | D | C | D | n.a. | D |
| S-Perillic Acid | B | C | A | B | B | D | C | D | n.a. | D | n.a.: not applicable (*A. brasiliensis* does not grow at pH > 7.0);
n.d.: not determined Compared to the free perillic acid the employment of sodium perillate and other alkali salts of perillic acid leads to a higher solubility in water-based systems at neutral pH. Due to the lack of the proton, alkali salts do not influence the pH in unbuffered water-based systems, thus pH-adjustment after compound addition is not necessary. Therefore, sodium perillate allows the application of higher concentrations and thus opens alternative formulation possibilities. Furthermore, as the salt of a weak acid (pKa=4.96), sodium perillate and other alkali salts possess a buffering effect, which can sup-port the pH-regulation of a final product.

1.1 In Vitro Activity

The antimicrobial activity of sodium perillate was examined in vitro using the microdilution method adapted from DIN EN ISO 20776-1:2006. R-Perillic acid and S-perillic acid were used as reference compounds. All experiments were done in 96-well plates in a final volume of 200 µL. Stock solutions of the investigated compounds were prepared in 25 mM buffer. The procedure was conducted as following: 4 µL of the particular stock solution were mixed with 196 µL culture medium containing a defined inoculum of the respective target strain. Sterile controls (not inoculated) and growth controls (buffer in-stead of compound added) were performed. All compound concentrations were tested in triplicate. The following strains were examined: *Escherichia coli* ATCC®8739, *Pseudomonas aeruginosa* ATCC®9027, *Stapyhlococcus aureus* ATCC®6538, *Candida albicans* ATCC®10231 and *Aspergillus brasiliensis* ATCC®16404. The following culture media were used: Mueller-Hinton II Bouillon (*Escherichia coli, Pseudomonas aeruginosa* and *Staphylococcus aureus*), yeast peptone dextrose (*Candida albicans*) and potato dextrose (*Aspergillus brasiliensis*). All culture media were buffered with 25 mM MES-buffer. For compound testing the plates were incubated at 37° C. (*Escherichia coli, Pseudomonas aeruginosa*

1.2 In Product Activity/Conservation Efficacy

The conservation efficacy of sodium perillate in a final product was determined using two different formulations:
a) an oil-water-emulsion pH 5.5 (example for a cosmetic product),
b) a water-based glucose solution at pH 3.5 (example for a non-carbonated soft drink).

Hereby, a defined inoculum of the test strains was added directly to the formulations. In order to examine product preservation by sodium perillate or perillic acid, the formulations were incubated at room temperature for 4 to 16 weeks, respectively. Samples were taken every 7 days and cell-forming units (cfu) were counted on agar plates.

Among others the following strains were used to determine the efficacy of sodium peril-late in an oil-water emulsion: *Escherichia coli* ATCC®8739, *Pseudomonas aeruginosa* ATCC®9027, *Stapyhlococcus aureus* ATCC®6538, *Candida albicans* ATCC®10231, and *Aspergillus brasiliensis* ATCC®16404.

Composition of an oil-water-emulsion (ingredient amounts according to the FDA-code):

| Ingredient | Amount [%] |
|---|---|
| Water | add 100 |
| Humectant | E |
| Thickener | F |
| Oil | C |
| Emulsifier | E |
| Sodium perillate | F-G |
| Active compound | E-F |

Table 2 Conservation efficacy testing of a typical cosmetic oil-water-emulsion at pH 5-6 supplemented with sodium perillate using five classical microbial test strains. All formulations were inoculated with a defined cell concentration and incubated over a time of 28 days at room temperature under standardized conditions. After 7, 14, 21 and 28 days samples were taken and the colony forming units (cfu) were calculated.

Conservation efficacy testing was performed using five microbial test strains: *Saccharomyces* sp., *Schizosaccharomyces* sp., *Asaia* sp., *Lactobacillus* sp., and *Aspergillus* sp. All formulations were inoculated with a defined cell concentration and incubated at room temperature under standardized conditions. After 7, 14, 21 and 28 days samples were taken and the colony forming units (cfu) were calculated and shown here.

| O/W emulsion Sodium perillate | CFU/mL at Sampling Timepoint | | | | | Reduced log-steps |
|---|---|---|---|---|---|---|
| Microbial strain | T0 | T7 | T14 | T21 | T28 | After T28 |
| E. coli | 1,680,000 | 53,500 | 190 | 370 | 1,430 | 3 |
| P. aeruginosa | 580,000 | 45,000 | 11,500 | 805 | 235 | 3 |
| S. aureus | 130,000 | 0 | 0 | 0 | 0 | 6 |
| C. albicans | 68,000 | 8,260 | 1,925 | 4,100 | 630 | 2 |
| A. brasiliensis | 11,000 | 13,000 | 2,270 | 2,900 | 170 | 2 |

| O/W emulsion Placebo | CFU/mL at Sampling Timepoint | | | | | |
|---|---|---|---|---|---|---|
| Microbial strain | T0 | T7 | T14 | T21 | T28 | |
| E. coli | 1,000,000 | 2,392,000 | 3,584,000 | 4,093,000 | 3,338,000 | 0 |
| P. aeruginosa | 75,000 | 1,056,000 | 3,156,000 | 3,306,000 | n.d. | 0 |
| S. aureus | 110,000 | 15,700 | 29,750 | n.d. | 63,250 | 0.5 |
| C. albicans | 17,000 | 1,504,000 | 1,600,000 | 2,025,000 | 4,145,000 | 0 |
| A. brasiliensis | 500 | 960 | 855 | 765 | 680 | 0 | n.d.: not determined

Among others the following species were used to determine the efficacy of sodium perillate in a water-based glucose formulation: *Saccharomyces* sp., *Schizosaccharomyces* sp., *Asaia* sp., *Lactobacillus* sp., and *Aspergillus* sp.

| | CFU/mL at Sampling Timepoint | | | | |
|---|---|---|---|---|---|
| Microbial strain | T0 | T7 | T14 | T21 | T28 |
| Aqueous formulation Sodium perillate | | | | | |
| *Saccharomyces* sp. | 10 | 23,900 | 52,900 | 530,000 | 470,000 |
| *Schizosaccharomyces* sp. | 55 | 350 | 3,265 | 4,990 | n.d. |
| *Asaia* sp. | 45 | 17,250 | 8,940 | 725 | 685 |
| *Lactobacillus* sp. | 10 | 10 | 56 | 340 | 910 |
| *Aspergillus* sp. | 10 | 0 | 0 | 0 | 0 |
| Aqueous formulation Placebo | | | | | |
| *Saccharomyces* sp. | 10 | 1,700,000 | 4,850,000 | 5,850,000 | 2,700,000 |
| *Schizosaccharomyces* sp. | 60 | 2,385,000 | 3,450,000 | 2,400,000 | 500,000 |
| *Asaia* sp. | 43 | 1,108,000 | 250,000 | 179,000 | 170,000 |
| *Lactobacillus* sp. | 10 | 3,770 | 459 | 750 | 1,700 |
| *Aspergillus* sp. | 5 | 110 | 35 | 41 | 41 | n.d.: not determined

Composition of a water-based glucose formulation (ingredient amounts according to the FDA-code):

| Ingredient | Amount [%] |
|---|---|
| Apple juice (sterile) | A |
| Water | A-B |
| Glucose | E |
| Sodium perillate | G |
| Citric acid | pH-adjustment |

Table 3 Illustration of cell reduction using sodium perillate in a typical aqueous formulation (juice matrix) for beverages pH 2.5-4 supplemented with sodium perillate.

Formulations Studies

The formulation of sodium perillate was performed with two different basic cosmetic formulation types: an oil-water-emulsion and a surfactant-containing formulation. For a comprehensive assessment the prepared formulations were stored at 4° C., 22-25° C. (room temperature) and 40° C. Additionally, respective formulations were subjected to a stress test (daily temperature change: 4° C., room temperature, 40° C.), were centrifuged and/or freezed for several times. Product stability was then evaluated with respect to the following criteria: physical stability, color change, smell and precipitation. Evaluations were performed monthly over a period of 6 months. In summary, all formulations with sodium perillate were physically stable, showed neither a discoloration compared to a respective placebo, nor a precipitation. All data are compiled in Table 4.

Table 4 Compilation of the formulation studies and the stability assessment of thereof. Data shown here have been recorded after 9 months of observation. All formulations were evaluated by comparing the criteria to a placebo formulation containing no sodium perillate.

| Formulation Type | Physical stability | Discoloration[a] | Smell[a] | Precipitation |
|---|---|---|---|---|
| Oil-water-emulsion | | | | |
| 4° C. | Stable | No | Corresponds | Not observed |
| 22-25° C. (rt) | Stable | No | Corresponds | Not observed |
| 40° C. | Stable | No | Corresponds | Not observed |
| Stress test | Passed | No | Corresponds | Not observed |
| 4° C., rt, 40° C. | Passed | No | Corresponds | Not observed |
| Centrifugation | Passed | No | Corresponds | Not observed |
| Freezing | Passed | No | Corresponds | Not observed |
| Surfactant-containing formulation | | | | |
| 4° C. | Stable | No | Corresponds | Not observed |
| 22-25° C. (rt) | Stable | No | Corresponds | Not observed |
| 40° C. | Stable | No | Corresponds | Not observed |
| Stress test | Passed | No | Corresponds | Not observed |
| 4° C., rt, 40° C. | Passed | No | Corresponds | Not observed |
| Centrifugation | Passed | No | Corresponds | Not observed |
| Freezing | Passed | No | Corresponds | Not observed |
| Water-oil-emulsion | | | | |
| 4° C. | Stable | No | Corresponds | Not observed |
| 22-25° C. (rt) | Stable | No | Corresponds | Not observed |
| 40° C. | Stable | No | Corresponds | Not observed |
| Stress test | Passed | No | Corresponds | Not observed |
| 4° C., rt, 40° C. | Passed | No | Corresponds | Not observed |
| Centrifugation | Passed | No | Corresponds | Not observed |
| Freezing | Passed | No | Corresponds | Not observed |

[a]In comparison to a placebo formulation containing no sodium perillate.

Composition of Formulations:

| Ingredient | Amount [% w/v] |
|---|---|
| Oil-Water Emulsion | |
| Aqua | 80.88 |
| Glycerol | 2 |
| Alkyl-acrylate crosspolymer | 0.27 |
| Sucrose stearate | 2.5 |
| Ethylhexyl palmitate | 6 |
| Dicaprylyl ether | 2 |
| Cetearyl isononanoate | 3 |
| Xanthan gum | 0.25 |
| Arginine | 3.0 |
| Perillic acid compound | 0.1 |
| Water-Oil Emulsion | |
| Aqua | 63.5 |
| Sorbitol | 4 |
| Allantoin | 0.2 |
| Magnesium sulfate | 1 |
| Polyglycerol-2 Dipolyhydroxystearate | 4 |
| Glyceryl oleate | 2 |
| Propyheptyl caprylate | 4 |
| Hexyl laurate | 3 |
| Cetearyl isononanoate | 6 |
| Capric triglyceride | 6 |
| Persea gratissima oil | 2 |
| Cara alba | 2.5 |
| Tocopherol acetate | 0.4 |
| Zinc stearate | 1 |
| Panthenol | 0.3 |
| Perillic acid compound | 0.1 |
| Surfactant-containing formulation | |
| Aqua | 58.2 |
| Sodium laureth sulfate | 30 |
| Cocoamidopropylbetain | 5 |
| Sodium cocoamphoacetate | 0.8 |
| Glycerol | 0.3 |
| Lauryl glucoside | 0.2 |
| Sodium cocoyl glutamate | 0.5 |
| Sodium lauryl gluaose carboxylate | 0.2 |
| Citric acid | 1.2 |
| Sodium chloride | 3.5 |
| Perillic acid compound | 0.1 |

1.4 Stability Investigation

Sodium perillate was prepared by adding a defined volume of a 0.1 M sodium hydroxide (NaOH) solution to perillic acid to give an aqueous solution of pH 7.0. The water was removed by evaporation resulting in a colorless solid. In order to investigate the stability of sodium perillate, the compound was stored for 12 months at 4° C., 22-25° C. (resemble room temperature) and 50° C. At certain time intervals all samples were examined and evaluated qualitatively using thin layer chromatography and quantitatively using gas and liquid chromatography. The results were compared to the stability of R perillic acid. Within the investigation period no degradation products of sodium perillate could be detected. These experiments highlight the long-term stability of sodium perillate.

Table 5 Recovery of sodium perillate measured by liquid chromatography (HPLC). Column: Phenomenex Luna O18. Method: 70% acetonitrile and 30% water, isocratic. Recovery values were calculated according to a calibration curve performed with sodium perillate in the range of 0.05-2 mM in acetonitrile. Detection was carried out by UV-light (DAD-detector) at 217 and 240 nm.

| | Recovery in % | | |
|---|---|---|---|
| Storage Temp. | 4° C. | 22-25° C. (RT) | 50° C. |
| $T_{start}$ | 99.6 | 99.3 | 99.3 |
| $T_{2\ months}$ | 99.7 | 99.1 | 99.4 |
| $T_{4\ months}$ | 99.2 | 99.5 | 99.2 |
| $T_{8\ months}$ | 99.2 | 99.7 | 99.2 |
| $T_{12\ months}$ | 99.4 | 99.3 | 99.3 |

The invention claimed is:

1. A composition comprising:
    at least one perillic acid compound, selected from the group consisting of perillic acid, and one or more salts of perillic acid, and
    water,
    wherein the composition has a pH in the range of from 2.5 to 6.5,
    wherein the perillic acid compound is present in an amount from about 0.001% (w/v) to about 0.2% (w/v) so that the composition is capable of maintaining the total amount of *Lactobacillus* sp. present in the composition below 1,000 cfu/mL after 28 days at 22-25° C.

2. The composition according to claim 1, comprising the perillic acid compound in an amount of at least 0.01% w/v.

3. The composition according to claim 1, wherein the perillic acid compound comprises a salt of perillic acid, wherein the salt comprises the ammonium salt, the alkali metal salt or the alkaline metal salt.

4. The composition according to claim 1, wherein the perillic acid compound comprises sodium perillate, potassium perillate, ammonium perillate, calcium perillate, magnesium perillate, and mixtures thereof.

5. The composition according to claim 1, wherein the pH is at least 3.

6. The composition according to claim 1, wherein the pH is from 4.5 to 6.5.

7. The composition according to claim 1, wherein the amount of water is at least 10% by weight relative to the total amount of the composition.

8. The composition according to claim 1, wherein the amount of water is at least 30% by weight relative to the total amount of the composition.

9. The composition according to claim 1, wherein the perillic acid compound is used in the form of its R-enantiomer, its S-enantiomer or any mixture thereof, including racemic mixtures.

10. The composition according to claim 1, wherein the composition comprises a foodstuff, food packaging, beverage, animal food, medicinal product, pharmaceutical product, cosmetic product, household product, plant protection, industrial or technical product.

11. The composition according to claim 1, wherein the composition comprises limonene in a concentration of less than 10 mM.

12. The composition according to claim 1, wherein the composition does not comprise any limonene in detectable amounts.

13. The composition according to claim 1, wherein the composition additionally comprises at least one antimicrobial compound.

14. The composition according to claim 1, wherein the range of said perillic acid is from about 0.000977% w/v to about 0.0099% w/v.

15. The composition according to claim 2, wherein the range of said perillic acid is from about 0.000977% w/v to about 0.0099% w/v.

16. The composition according to claim 5, wherein the range of said perillic acid is from about 0.000977% w/v to about 0.0099% w/v.

17. The composition according to claim 6, wherein the range of said perillic acid is from about 0.000977% w/v to about 0.0099% w/v.

* * * * *